United States Patent
Oliner et al.

(10) Patent No.: US 6,177,248 B1
(45) Date of Patent: Jan. 23, 2001

(54) DOWNSTREAM GENES OF TUMOR SUPPRESSOR WT1

(75) Inventors: Jonathan Oliner, Mountain View; Vivi Truong, San Jose, both of CA (US); Daniel Haber, Chestnut Hill; Sean Lee, Malden, both of MA (US)

(73) Assignee: Affymetrix, Inc., Santa Clara, CA (US)

( * ) Notice: Under 35 U.S.C. 154(b), the term of this patent shall be extended for 0 days.

(21) Appl. No.: 09/256,301

(22) Filed: Feb. 24, 1999

(51) Int. Cl.[7] ............................. C12Q 1/68; C12N 15/00; C07H 21/02
(52) U.S. Cl. .............................. 435/6; 435/440; 536/23.1
(58) Field of Search .................................. 536/23.1, 24.5; 435/440, 5, 6, 94

(56) References Cited

U.S. PATENT DOCUMENTS 5,700,637 12/1997 Southern .

FOREIGN PATENT DOCUMENTS

89/10977 11/1989 (WO) .

OTHER PUBLICATIONS

Microsoft Corporation, "Microsoft Excel User's Guide", 1992–1993, chapter 9 and pp. 307–316.*
Goodyer P et al, "Repression of the retinoic acid receptor–alpha gene by the Wilms' tumor supressor gene product, wt1", Oncogene (1995) 10, pp. 1125–1129.*
Schena M et al, "Quantitative monitoring of gene expression patterns with a complementary DNA microarray", Science, vol. 270, Oct. 20, 1995, pp. 467–470.*
Roberts CT, "control of insulin–like growth factor (IGF) action by regulation of IGF–I receptor expression", Endocrine Journal, 1996, 43(suppl.), S49–S55.*
Mastick CC et al, "Insulin stimulates the tyrosine phosphorylation of caveolin", J of Cell Biology, Jun. 1995, 129(6), pp. 1523–1531.*
Christoph Englert et al. "Induction of p. 21 by the Wilms' Tumor Suppressor Gene WT1[1]" Cancer Research 57: 1429–1434, Apr. 15, 1997.
Christoph Englert et al. "WT1 Suppresses Synthesis of the Epidermal Growth Factor Receptor and Induces Apoptosis" The EMBO Journal vol. 14, No. 19 pp. 4462–4675 1995.
Maheswaran et al. "Inhibition of cellular proliferation by the Wilms tumor suppressor WT1 requires association with the inducible chaperone Hsp70" Genes and Development 12:1108–1120 1998.

* cited by examiner

Primary Examiner—John S. Brusca
Assistant Examiner—Stephen Siu
(74) Attorney, Agent, or Firm—Banner & Witcoff Ltd.

(57) ABSTRACT

Methods are provided for diagnosing cancers, drug-screening, and functionally analyzing mutations involving the WT1 gene. The methods involve use of the newly identified set of genes which are regulated by WT1 as well as by the set of genes which are regulated by WT1 fusions to EWS. Monitoring expression levels of these sets of genes can be used as an indicator of the genetic status of the gene. It can also identify which have similar effects on downstream genes.

26 Claims, No Drawings

DOWNSTREAM GENES OF TUMOR SUPPRESSOR WT1

BACKGROUND OF THE INVENTION

Many biological functions are accomplished by altering the expression of various genes through transcriptional (e.g. through control of initiation, provision of RNA precursors, RNA processing, etc.) and/or translational control. For example, fundamental biological processes such as cell cycle regulation, cell differentiation and cell death, are often characterized by the variations in the expression levels of groups of genes.

Gene expression is also associated with pathogenesis. For example, the lack of sufficient expression of functional tumor suppressor genes and/or the over expression of oncogene/protooncogenes could lead to tumorigenesis (Marshall, *Cell,* 64: 313–326 (1991); Weinberg, Science, 254: 1138–1146 (1991), incorporated herein by reference for all purposes). Thus, changes in the expression levels of particular genes (e.g. oncogenes or tumor suppressors) serve as signposts for the presence and progression of various diseases. There is a need in the art for discovering which genes are affected by particular tumor suppressors and oncogenes, so that they can be used diagnostically as well as in the search for new therapeutics.

SUMMARY OF THE INVENTION

It is an object of the invention to provide methods for identifying a functional mutation in a WT1 gene.

It is another object of the invention to provide methods for identifying a EWS-WT1 gene fusion.

It is still another object of the invention to provide an in-cell assay to test the biological effect of a WT1 mutation.

It is yet another object of the invention to provide methods to detect a WT1 mutation or a EWS-WT1 fusion using a computer.

It is a further object of the invention to provide methods to diagnose neoplasia.

It is another object of the invention to provide methods for identifying drugs useful for treating neoplasias.

These and other objects of the invention are provided by one or more of the following embodiments. In one embodiment a method is provided for detecting a WT1 gene functional mutation in target cells. Expression of at least three down-stream genes of WT1 is detected in a sample of (a) target cells, and (b) reference cells having a wild-type WT1 gene. The reference cells are otherwise substantial similar to the target cells. The down-stream genes are up- or down-regulated by the wild-type WT1 gene. The expression of the down-stream genes in the target cells and the reference cells is compared; a difference in the expression between the target cells and reference cells suggests a WT1 functional mutation in the target cells.

According to yet another embodiment a method is provided for detecting a EWS-WT1 gene fusion in target cells. Expression of one or more down-stream genes of an EWS-WT1 fusion is detected in a sample of (a) target cells, and (b) reference cells having a wild-type EWS and WT1 gene. The reference cells are otherwise substantially similar to the target cells. The down-stream genes are up- or down-regulated by the wild-type EWS and WT1 gene. The expression of the down-stream genes in the target cells and the reference cells is compared. A difference in the expression between the target cells and reference cells suggests a EWS-WT1 fusion in the target cells.

Another aspect of the invention is an in-cell functional assay for a WT1 sequence alteration. The expression is detected of at least three down-stream genes in a target sample from target cells having a WT1 sequence alteration and in a reference sample from reference cells having a wild-type WT1 gene. The reference cells are otherwise substantially similar to the target cells. The down-stream genes are up- or down-regulated by the wild-type WT1 gene. The expression in the target sample is compared to the expression in the reference sample. A difference in the expression between the two samples suggests that the WT1 sequence alteration affects the biological function of WT1.

According to another aspect of the invention a method is provided for detecting a mutation in a target WT1 gene using a computer. Wild-type expression data of at least three down-stream genes in a wild-type sample containing a wild-type WT1 gene is input into a computer. The down-stream genes are transcriptionally regulated by the wild-type WT1 gene. Target expression data of the plurality of down-stream genes in a target sample containing the target WT1 gene is also input into a computer. The target and wild-type expression data are compared to determine differences. Differences suggest a mutation in the target WT1 gene.

In still another embodiment a method is provided for detecting a translocation fusing EWS and WT1 genes using a computer. Wild-type expression data of a plurality of down-stream genes in a wild-type sample containing wild-type EWS and WT1 genes is input into a computer. The down-stream genes are transcriptionally regulated by a EWS-WT 1 fusion protein. Target expression data of the plurality of down-stream genes in a target sample which is being tested for the presence of a EWS-WT1 fusion protein is also input into a computer. The target and wild-type expression data are compared to determine differences. Such differences suggest a translocation fusing the EWS and WT1 genes.

Another embodiment of the invention provides a method of diagnosing neoplasia of a test cell. A transcription indicator of a test cell is hybridized to a set of nucleic acid probes. The transcription indicator is selected from the group consisting of mRNA, cDNA and cRNA The set of nucleic acid probes comprises a plurality of nucleic acid molecules each of which is a portion of a gene which is activated by or repressed by WT1 selected from the group consisting of: natural killer cells protein 4 precursor (M59807), heat shock protein HSP70B (X51758), 90 K product (H17969), heat shock 70 kd protein 1 (T66307), procollagen alpha 1 (T51558), cysteine protease inhibitor from radiated keratinocytes (X05978), brain natriuretic protein (BNP) (M31766), leukemia virus receptor 1 (GLVR1) (20859), type 1 cytoskeletal 17 keratin (R71870), purine nucleoside phosphorylase (T47964), adrenomedullin (D14874), gravin (M96322), jun-B (X51345), elongation factor 1 alpha-2 (X79490), homeotic gene regulator (R16977), clone 9112 (X57348), interferon gamma treatment inducible mRNA (M26683), transmembrane receptor protein (Z17227) and mitochondrial phosphate carrier protein (R49231). Amounts of transcription indicator which hybridize to each of the set of nucleic acid probes are detected. A test cell is identified as neoplastic if (1) hybridization of the transcription indicator of the test cell to a probe which is a WT1-activated gene is lower than hybridization using a transcription indicator from a normal cell, or (2) hybridization of the transcription indicator of the test cell to a probe which a WT1-repressed gene is higher than hybridization using a transcription indicator from a normal cell.

A further aspect of the invention is provided by a method of identifying anti-cancer drugs. A test compound is contacted with a human cell. The effect of the test compound on the expression by the cell of at least one WT1 up- or down-regulated gene is determined. The regulated gene is selected from the group consisting of: natural killer cells protein 4 precursor (M59807), heat shock protein HSP70B (51758), 90 K product (H17969), heat shock 70 kd protein 1 (T66307), procollagen alpha 1 (T51558), cysteine protease inhibitor from radiated keratinocytes (X05978), brain natriuretic protein (BNP) (M31766), leukemia virus receptor 1 (GLVR1) (L20859), type 1 cytoskeletal 17 keratin, purine nucleoside phosphorylase (T47964), adrenomedullin (D14874), gravin (M96322), jun-B (X51345), elongation factor 1 alpha-2 (X79490), homeotic gene regulator (R16977), clone 9112 (X57348), interferon gamma treatment inducible mRNA (M26683), transmembrane receptor protein (Z17227) and mitochondrial phosphate carrier protein (R49231). A test compound is identified as a potential anti-cancer drug if it increases expression of at least one WT1 up-regulated gene or decreases expression of a WT1 down-regulated gene in the human cell.

Another aspect of the invention is a method of diagnosing neoplasia of a test cell. A transcription indicator of a test cell is hybridized to a set of nucleic acid probes. The transcription indicator is selected from the group consisting of mRNA, cDNA and cRNA. The set of nucleic acid probes comprises a plurality of nucleic acid molecules each of which is a portion of a gene which is activated by or repressed by a EWS-WT 1 fusion protein. Amounts of transcription indicator which hybridize to each of the set of nucleic acid probes are detected.

A test cell is identified as neoplastic if (1) hybridization of the transcription indicator of the test cell to a probe which is a EWS-WT1-activated gene is lower than hybridization using a transcription indicator from a normal cell, or (2) hybridization of the transcription indicator of the test cell to a probe which a EWS-WT1-repressed gene is higher than hybridization using a transcription indicator from a normal cell.

According to still another embodiment of the invention a method of identifying anti-cancer drugs is provided. A test compound is contacted with a human cell. Expression of an EWS-WT1 up-regulated gene or a EWS-WT1 down-regulated gene is determined. A test compound is identified as a potential anti-cancer drug if it decreases expression of a EWS-WT1 up-regulated genes or increases expression of a EWS-WT1 down-regulated gene in the human cell.

A method is also provided for detecting a WT1 gene functional mutation in target cells. Expression of at least one down-stream gene of WT1 is detected in a sample of (a) target cells, and (b) reference cells having a wild-type WT1 gene. The reference cells are otherwise substantially similar to the target cells. The down-stream genes are selected from the group consisting of: natural killer cells protein 4 precursor (M59807), folate binding protein (M25317), HALPHA44 gene for alpha-tubulin (X06956), heat shock protein HSP70B (X51758), 90 K product (17969), heat shock 70 kd protein 1 (T66307), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin, tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), elongation factor 1 alpha-2 (X79490), homeotic gene regulator (R16977), clone 9112 (X57348), interferon gamma treatment inducible mRNA (M26683), transmembrane receptor protein (Z17227) mitochondrial phosphate carrier protein (R49231), and caveolin. The expression of the at least one down-stream gene in the target cells and the reference cells is compared. A difference in the expression between the target cells and reference cells suggests a WT1 functional mutation in the target cells.

An in-cell functional assay for a WT1 sequence alteration is also provided by the present invention. Expression is detected in a target sample from target cells having a WT1 sequence alteration and in a reference sample from reference cells having a wild-type WT1 gene of at least one down-stream gene selected from the group consisting of: natural killer cells protein 4 precursor (M59807), folate binding protein (M25317), HALPHA44 gene for alpha-tubulin (X06956), heat shock protein HSP70B (X51758), 90 K product (H17969), heat shock 70 kd protein 1 (T66307), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin, tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), elongation factor 1 alpha-2 (X79490), homeotic gene regulator (R16977), clone 9112 (X57348), interferon gamma treatment inducible mRNA (M26683), transmembrane receptor protein (Z 17227), caveolin and mitochondrial phosphate carrier protein (R49231). The reference cells are otherwise substantially similar to the target cells. The down-stream genes are up- or down-regulated by the wild-type WT1 gene. Expression in the target sample is compared to the expression in the reference sample. A difference in the expression between the two samples suggests that the WT1 sequence alteration affects the biological function of WT1.

Another embodiment of the invention provides a method for detecting a mutation in a target WT1 gene using a computer. Wild-type expression data of at least one WT1-down-stream gene in a wild-type sample containing a wild-type WT1 gene is input into a computer. The down-stream gene is selected from the group consisting of: natural killer cells protein 4 precursor (M59807), folate binding protein (M25317), HALPHA44 gene for alpha-tubulin (X06956), heat shock protein HSP70B (X51758), 90K product (H17969), heat shock 70 kd protein 1 (T66307), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin, tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), elongation factor 1 alpha-2 (X79490), homeotic gene regulator (R 16977), clone 9112 (X57348), interferon gamma treatment inducible mRNA (M26683), transmembrane receptor protein (Z17227), caveolin, and mitochondrial phosphate carrier protein (R49231). Target expression data of the plurality of down-stream genes in a target sample containing the target WT1 gene is also input into a computer. The target and wild-type expression data are compared to determine differences. Such differences suggest a mutation in the target WT1 gene.

According to yet another aspect of the invention a method of diagnosing neoplasia of a test cell is provided. Expression levels are determined in a test cell and in a control cell of at least one gene which is activated by or repressed by WT1. The genes are selected from the group consisting of: natural killer cells protein 4 precursor (M59807), heat shock protein HSP70B (X 51758), 90 K product (H17969), heat shock 70 kd protein 1 (T66307), procollagen alpha 1 (T51558), cysteine protease inhibitor from radiated keratinocytes (X05978), brain natriuretic protein (BNP) (M31766), leukemia virus receptor 1 (GLVR1) (L20859), type 1 cytoskeletal 17 keratin (R71870), purine nucleoside phosphorylase (T47964), adrenomedullin (D14874), gravin (M96322), jun-B (X51345), elongation factor 1 alpha-2 (X79490), homeotic gene regulator (R16977), clone 9112 (X57348), interferon gamma treatment inducible mRNA (M26683), transmembrane receptor protein (Z17227) and mitochondrial phosphate carrier protein (R49231). The determined expression levels in the test cell is compared to the determined expression levels in the control cell. The test cell is identified as neoplastic if (1) the level of expression of at least one of the genes which is a WT1-activated gene is lower in the test cell than in the control cell, or (2) the level of expression of at least one of the genes which is WT1-repressed is higher in the test cell than in the control cell.

Another aspect of the invention provides a method of diagnosing neoplasia of a test cell. Expression levels in a test cell and in a control cell are determined of at least one gene which is activated by or repressed by a EWS-WT1 fusion protein. The determined expression levels in the test cell are compared to the determined expression levels in the control cell. A test cell is identified as neoplastic if (1) expression in the test cell of a EWS-WT1-activated gene is lower than expression in a normal cell, or (2) expression in the test cell of a EWS-WT1-repressed gene is higher than expression in the normal cell.

Also provided is an additional method of diagnosing neoplasia of a test cell. Expression levels are determined in a test cell and in a control cell of at least three genes which are activated by or repressed by WT1. The determined expression levels in the test cell are compared to the determined expression levels in the control cell. A test cell is identified as neoplastic if (1) expression in the test cell of a WT1-activated gene is lower than expression in a normal cell, or (2) expression in the test cell of a WT1-repressed gene is higher than expression in the normal cell.

DETAILED DESCRIPTION OF THE INVENTION

It is a discovery of the present inventors that WT1 regulates the transcription of a set of genes, the size of the set being far greater than previously suggested. Sets of genes have been identified which are up-regulated and down-regulated by WT1, the latter set being far smaller. In addition, genes have been identified which are up-regulated by the EWS-WT1 gene fusion caused by a translocation. This translocation occurs in desmoplastic round cell tumors, such as Ewing's Sarcomas. Identification of these sets of genes permits their use in a variety of diagnostic and analytical methods. It also permits their use to screen compounds for drugs which have the same or similar effects as WT1 and for drugs which have the opposite effect from the EWS-WT1 gene fusion.

Table 1 shows the genes which are regulated by WT1. Of those genes only caveolin and elongation factor 1 alpha-2 are down-regulated by WT1. The others are up-regulated by WT1. Table 2 shows a subset of the WT1-regulated genes which were known to have a previously suggested link to cancer and what that link is. Table 3 shows the genes which are regulated by the EWS-WT1 fusion gene. All of these genes are up-regulated by the fusion gene. Other genes are undoubtedly regulated by these genes, and they can be identified using similar techniques to those described in the example. Alternatively, other techniques such as Serial Analysis of Gene Expression (SAGE) can be used to identify regulated genes which may not yet have been identified or made part of the public databases.

Expression of genes which are regulatorily downstream of WT1 or EWS-WT1 can be monitored by any techniques known in the art. These include but are not limited to the use of SAGE, hybridization to probes on an array, Western blot, Northern blot, dot blot, slot blot, ELISA, radioimmunoassay. Any technique which can be used to quantitate a gene product, whether mRNA or protein, can be used. The methods of the present invention predominantly analyze changes in a test sample as compared to a control sample. Precise quantitation need not be accomplished. In many cases comparisons will suffice without ever determining an absolute amount of a gene product.

Target cells, as used in the present invention are those cells which are being tested. Typically they are of an unknown mutational status. In some instances, a mutation is identified in the target cells, but its functional effect is unknown. Reference cells are preferably as similar as possible to the target cells, to permit the easiest detection of differences which are due to the WT1 gene or the EWS-WT1 gene. Reference cells typically comprise wild-type WT1 alleles. Often the reference cells are taken from the same individual and from the tissue adjacent to a tumor sample which is being tested.

Differences between target cells and reference cells may be small or large. Some small differences may be very reproducible and therefore useful. For other purposes, large differences may be desirable for ease of detection. For some assays it may be useful to set threshold levels of change. For some purposes such threshold levels may be 0.5, 2, 3, 5, 7, or 10 fold. This may depend on the technique being used for detection as well as on the number of genes which are being tested. One of skill in the art can readily set threshold levels which are preferred in a particular methodological context.

The number of downstream genes analyzed can vary depending, for example, on the magnitude of induced changes and their reproducibility. In some instances, larger numbers of genes may be analyzed to more accurately reflect a WT1 change, since other genes may also affect expression of a particular gene being analyzed. Typically at least 1, 2, 3, 4, 5, 7, 10, or 15 downstream genes of WT1 or EWS-WT1 are analyzed. Analysis of a number of genes greater than 1 can be accomplished simultaneously, sequentially, or cumulatively.

Computers can be used in the present invention to store data, to perform mathematical comparisons, to store results. Data can be manually input or may be fed from other machines, such as optical scanners, scintillation counters, and the like. High through-put screens can thus be efficiently run and analyzed.

I. Definitions

Hybridizing specifically to: The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) DNA or RNA.

mRNA or transcript: The term "mRNA" refers to transcripts of a gene. Transcripts are RNA including, for example, mature messenger RNA ready for translation, products of various stages of transcript processing. Transcript processing may include splicing, editing and degradation.

Nucleic Acid: The terms "nucleic acid" or "nucleic acid molecule" refer to a deoxyribonucleotide or ribonucleotide polymer in either single-or double-stranded form, and unless otherwise line would encompass analogs of natural nucleotide that can function in a similar manner as naturally occurring nucleotide. A n oligonucleotide is a single-stranded nucleic acid of 2 to n bases, where n may be greater than 500 to 1000. Nucleic acids may be cloned or synthesized using any technique known in the art. They may also include non-naturally occurring nucleotide analogs, such as those which are modified to improve hybridization and peptide nucleic acids.

Nucleic acid encoding a regulatory molecule: The regulatory molecule may be DNA, RNA or protein. Thus for example DNA sites which bind protein or other nucleic acid molecules are included within the class of regulatory molecules encoded by a nucleic acid.

Probe: As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

Target nucleic acid: The term "target nucleic add" refers to a nucleic acid (often derived from a biological sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

Stringent conditions: The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Subsequence: "Subsequence" refers to a sequence of nucleic acids that comprise a part of a longer sequence of nucleic acids.

Thermal melting point (Tm): The Tm is the temperature, under defined ionic strength, pH, and nucleic acid concentration, at which 50% of the probes complementary to the target sequence hybridize to the target sequence at equilibrium. As the target sequences are generally present in excess, at Tm, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotide). Stringent conditions may also be achieved with the addition of destabilizing agents such as formamide.

Quantifying: The term "quantifying" or "quantitating" when used in the context of quantifying transcription levels of a gene can refer to absolute or to relative quantification. Absolute quantification may be accomplished by inclusion of known concentration(s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Up-stream or down-stream gene. If the expression of a first gene is regulated by a second gene, the second gene is called an "up-stream gene" for the first gene and the first gene is the "down-stream" gene of the second gene. The regulation of the first gene by second gene could be through trans-activation. For example, the first gene encodes a transcriptional factor that controls the expression of the second gene. The regulation can also be exerted by a cis-acting mechanism. For example, the first gene is in the proximity of the second gene and exerts a positional effect on the expression of the second gene. In this case, the first gene does not have to be expressed in order to have an influence on the second gene.

Activity of a gene is reflected by the activity of its product(s): the proteins or other molecules encoded by the gene. Those product molecules perform biological functions. Directly measuring the activity of a gene product is, however, often difficult for certain genes. Instead, the immunological activities or the amount of the final product(s) or its peptide processing intermediates are determined as a measurement of the gene activity. More frequently, the amount or activity of intermediates, such as transcripts, RNA processing intermediates, or mature mRNAs are detected as a measurement of gene activity.

In many cases, the form and function of the final product (s) of a gene is unknown. In those cases, the activity of a gene is measured conveniently by the amount or activity of transcript(s), RNA processing intermediate(s), mature mRNA(s) or its protein product(s) or functional activity of its protein product(s).

Any methods that measure the activity of a gene are useful for at least some embodiments of this invention. For example, traditional Northern blotting and hybridization, nuclease protection, RT-PCR and differential display have been used for detecting gene activity. Those methods are useful for some embodiments of the invention. However, this invention is most useful in conjunction with methods for detecting the expression of a large number of genes.

High-density arrays are particularly useful for monitoring the expression control at the transcriptional, RNA processing and degradation level. The fabrication and application of high-density arrays in gene expression monitoring have been disclosed previously in, for example, WO 97/10365, WO 92/10588, U.S. application Ser. No. 08/72,376 filed Dec. 23, 1996; Ser. No. 08/529,115 filed on Sep. 15, 1995 now U.S. Pat. No. 6,040,138; Ser. No. 08/168,904 filed Dec. 15, 1993 now abandoned; Ser. No. 07/624,114 filed on Dec. 6, 1990 now abandoned, Ser. No. 07/362,901 filed Jun. 7, 1990 now abandoned, all incorporated herein for all purposed by reference. In some embodiment using high-density arrays, high-density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high-density array of oligonucleotides and then the amount of target nucleic acids hybridized to each probe in the array is quantified. One preferred quantifying method is to use confocal microscope and fluorescent labels. The Gene-Chip® system (Affymetrix, Santa Clara, Calif.) is particularly suitable for quantifying the hybridization; however, it will be apparent to those of skill in the art that any similar systems or other effectively equivalent detection methods can also be used.

High-density arrays are suitable for quantifying a small variations in expression levels of a gene in the presence of a large population of heterogeneous nucleic acids. Such high-density arrays can be fabricated either by de novo synthesis on a substrate or by spotting or transporting nucleic acid sequences onto specific locations of substrate. Nucleic acids are purified and/or isolated from biological materials, such as a bacterial plasmid containing a cloned segment of sequence of interest. Suitable nucleic acids are also produced by amplification of templates. As a nonlimiting illustration, polymerase chain reaction, and/or in vitro transcription, are suitable nucleic acid amplification methods.

Synthesized oligonucleotide arrays are particularly preferred for this invention. Oligonucleotide arrays have numerous advantages, as opposed to other methods, such as efficiency of production, reduced intra- and inter array variability, increased information content and high signal-to-noise ratio.

Preferred high-density arrays for gene function identification and genetic network mapping comprise greater than about 100, preferably greater than about 1000, more preferably greater than about 16,000 and most preferably greater than 65,000 or 250,000 or even greater than about 1,000,000 different oligonucleotide probes, preferably in less than 1 $cm^2$ of surface area. The oligonucleotide probes range from about 5 to about 50 or about 500 nucleotides, more preferably from about 10 to about 40 nucleotide and most preferably from about 15 to about 40 nucleotides in length.

Generally methods of monitoring gene expression involve (a) providing a pool of target nucleic acids comprising RNA transcript(s) of one or more target gene(s), or nucleic acids derived from the RNA transcript(s); (b) hybridizing the nucleic acid sample to a high-density array of probes and (c) detecting the hybridized nucleic acids and calculating a relative and/or absolute expression (transcription, RNA processing or degradation) level.

(A) Providing a Nucleic Acid Sample

One of skill in the art will appreciate that it is desirable to have nucleic samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Transcripts, as used herein, may include, but not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, such sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (dT) column contains RNA molecules with poly (A) tails. Those polyA$^+$ RNA molecules could be mature mRNA, RNA processing intermediates, nascent transcripts or degradation intermediates.

Biological samples may be of any biological tissue or fluid or cells from any organism. Frequently the sample will be a "clinical sample" which is a sample derived from a patient. Clinical samples provide a rich source of information regarding the various states of genetic network or gene expression. Some embodiments of the invention are employed to detect mutations and to identify the phenotype of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase is inhibited or destroyed by heat treatment followed by proteinase treatment.

Methods of isolating total mRNA are also well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993)).

In a preferred embodiment, the total RNA is isolated from a given sample using, for example, an acid guanidinium-phenol-chloroform extraction method and polyA$^+$ mRNA is isolated by oligo(dT) column chromatography or by using (dT) on magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology,* F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high-density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skilled in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications,* Innis et al., Academic Press, Inc. N.Y., (1990).

Other suitable amplification methods include, but are not limited to polymerase chain reaction (PCR) Innis, et al., *PCR Protocols. A guide to Methods and Application.* Academic Press, Inc. San Diego, (1990)), ligase chain reaction (LCR) (see Wu and Wallace, *Genomics,* 4: 560 (1989), Landegren, et al., *Science,* 241: 1077 (1988) and Barringer, et al., *Gene,* 89: 117 (1990), transcription amplification (Kwoh, et al., *Proc. Natl. Acad. Sci. USA,* 86: 1173 (1989)), and self-sustained sequence replication (Guatelli, et al, *Proc. Nat. Acad. Sci. USA,* 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. A one-tube mRNA capture method may be used to prepare poly(A)$^+$ RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo(dT) and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra) and this particular method is described in detail by Van Gelder, et al., *Proc. Natl. Acad. Sci. USA,* 87: 1663–1667 (1990) who demonstrate that in vitro amplification according to this method preserves the relative frequencies of the various RNA transcripts. Moreover, Eberwine et al. *Proc. Natl. Acad Sci. USA,* 89: 3010–3014 provide a protocol that uses two rounds of amplification via in vitro transcription to achieve greater than $10^6$ fold amplification of the original starting material, thereby permitting expression monitoring even where biological samples are limited.

(B) Hybridizing nucleic acids to high-density arrays

1. Probe design

One of skill in the art will appreciate that an enormous number of array designs are suitable for the practice of this invention. The high-density array will typically include a number of probes that specifically hybridize to the sequences of interest. In addition, in a preferred embodiment, the array will include one or more control probes.

The high-density array chip includes "test probes." Test probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiments, test probes are double or single strand DNA sequences. DNA sequences are isolated or cloned from nature sources or amplified from nature sources using nature nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high-density array can contain a number of control probes. The control probes fall into three categories referred to herein as 1) normalization controls; 2) expression level controls; and 3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (ie. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (I(PM)-I(MM)) provides a good measure of the concentration of the hybridized material.

The high-density array may also include sample preparation/amplification control probes. These are probes that are complementary to subsequences of control genes selected because they do not normally occur in the nucleic acids of the particular biological sample are assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

In a preferred embodiment, oligonucleotide probes in the high-density array are selected to bind specifically to the nucleic acid target to which they are directed with minimal non-specific binding or cross-hybridization under the particular hybridization conditions utilized. Because the high-density arrays of this invention can contain in excess of 1,000,000 different probes, it is possible to provide every probe of a characteristic length that binds to a particular nucleic acid sequence.

In addition, in a preferred embodiment, expression monitoring arrays are used to identify the presence and expression (transcription) level of genes which are several hundred base pairs long. For most applications it would be useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

As disclosed in U.S. application Ser. No. 08/772,376, probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high-density array.

2. Hybridization

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (eg., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6× SSPE-T at 37 C. (0.005% Triton X-100) to ensure hybridization and then subsequent washes are performed at higher stringency (e.g., 1 × SSPE-T at 37 C.) to eliminate mismatched hybrid duplexes. Successive washes may be performed at increasingly higher stringency (e.g., down to as low as 0.25 × SSPE-T at 37 C. to 50 C.) until a desired level of hybridization specificity is obtained. In another preferred embodiment 1 × MES buffer is used. The buffer comprises 0.1 M 2-[N-Morpholinio]ethanesulfonic acid, 1.0 NaCl, and 0.01 % Triton-X 100™. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an army which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology, Vol. 24: Hybridization With Nucleic Acid Probes*, P. Tijssen, ed. Elsevier, N.Y., (1993)).

(C) Signal Detection

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. One particular preferred methods uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high-density array are known to those of skill in the art. Thus, for example, where a colorimetric label is used, simple visualization of the label is sufficient. Where a radioactive labeled probe is used, detection of the radiation (e.g. with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high-density array. Similarly, the microscope may be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No: 5,143,854, PCT Application Ser. No. 20 92/10092, and copending U.S. application Ser. No. 08/195,889 filed on Feb. 10, 1994now U.S. Pat. No. 5,631,734. Use of laser illumination in conjunction with automated confocal microscopy for signal detection permits detection at a resolution of better than about 100 $\mu$m, more preferably better than about 50 $\mu$m, and most preferably better than about 25 $\mu$m.

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high-density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g. <1 pM) will show a very weak signal. At some low level of concentration, the signal becomes virtually indistinguishable from background. In evaluating the hybridization data, a threshold intensity value may be selected below which a signal is not counted as are essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal.

In addition, the provision of appropriate controls permits a more detailed analysis that controls for variations in hybridization conditions, cell health, non-specific binding and the like. Thus, for example, in a preferred embodiment, the hybridization array is provided with normalization controls. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplification control probes (e.g., the Bio B probes). The resulting values may be multiplied by a constant value to scale the results.

As indicated above, the high-density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control both show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

In some preferred embodiments, a computer system is used to compare the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes.

After the system compares the hybridization intensity of the perfect match and mismatch probes, the system indicates expression of the gene. As an example, the system may indicate to a user that the gene is either present (expressed), marginal or absent (unexpressed). Specific procedures for data analysis is disclosed in U.S. application Ser. No. 08/772,376, previously incorporated for all purposes.

In addition to high-density nucleic acid arrays, other methods are also useful for massive gene expression monitoring. Differential display, described by Liang, P. and Pardee, A. B. (Differential Display of eukaryotic messenger RNA by means of the polymerase chain reaction. *Science* 257:967–971, 1992, incorporated herein by reference for all purposes) provides a useful mean for distinguishing gene expression between two samples. Serial analysis of gene expression, described by Velculescu et al. (Serial Analysis of Gene Expression. *Science,* 270:484–487, 1995, incorporated herein by reference for all purposes) provides another method for quantitative and qualitative analysis of gene expression. Optical fiber oligonucleotide sensors, described by Ferguson et al. (A Fiber-optic DNA biosensor microarray for the analysis of gene expression. Nature-Biotechnology 14:1681–1684, 1996), can also be used for gene expression monitoring.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

EXAMPLES

To address the functional properties of WT1 and EWS-WT1 and examine their effects on endogenous target genes, we developed cells in which a tightly regulated inducible promoter allowed expression of the full length protein. Forced expression of WT1 and EWS-WT1 in these cells triggered apoptosis. Oligonucleotide array-based expression profiling revealed a small number of genes exhibiting altered expression following WT1 and EWS-WT1 induction.

To study the functional properties of WT1 and EWS-WT1, we established inducible, tetracyline-regulated expression (Gossen and Bujard, 1992) of WT1 and EWS-WT1 in U2OS osteosarcoma cells. We searched for endogenous genes whose expression levels might be altered following inducible expression of WT1 and EWS-WT1 . Messenger RNA was isolated from cells at 12 hrs following WT1 and EWS-WT1 induction, biotinylated, and hybridized to high-density oligonucleotide arrays representing 6,800 known transcripts and expressed sequence tags (Lockhart et al., 1996; Wodicka et al., 1997). A gene was considered a candidate WT1 and EWS-WT1 target if it was reproducibly induced or repressed in at least two different experimental replicates following WT1 and EWS-WT1 induction, and it exhibited an expression changes of at least 3-fold.

In this so-called "tet-off" induction system, the recombinant gene is induced by withdrawal of tetracycline from the tissue culture medium. The purpose of these studies was to identify candidate functional mediators (CFMs) of these tumor suppressors. Upon induction of WT1 or EWS-WT1 expression, we identified 28 and 17 endogenous genes, respectively (of 7000 genes monitored), that displayed reproducible expression changes of 3-fold or greater.

By generating cell lines with tightly regulated inducible expression of WT1 and EWS-WT1, we have identified downstream pathways that are likely to contribute to its function as a tumor suppressor.

Hybridization-Based Assay for Generating Expression Profiles

Messenger RNA levels are determined by hybridization of complete mRNA populations to sets of arrays containing hundreds of thousands of chemically synthesized oligonucleotides . The oligonucleotides are synthesized in situ on glass supports using light-directed, solid-phase combinatorial chemistry. Because the arrays are designed and synthesized based on sequence information alone, they provide a direct link between genomic sequence and measurements of differential gene expression. The arrays measure 1.28×1.28 cm and contain more than 65,000 50×50 micron synthesis features. Each synthesis feature consists of more than $10^7$ copies of a particular 25-mer oligonucleotide.

For each mRNA sample, the expression levels of 6,800 full-length human genes will be monitored. The full set of oligonucleotides covering these genes is divided over 4 different arrays, comprising a total area of approximately one square inch. For each gene, approximately 20 complementary 25-mers are chosen based on automated selection criteria. The criteria include tests for sequence uniqueness relative to the rest of the genome and the absence of sequence features (e.g., self-complementarity or clusters of single nucleotides) that have been determined to adversely affect hybridization behavior on arrays. The use of sets of oligonucleotides for each gene provides redundancy in the detection and analysis of the data, ≈tigates the potentially confounding effects of occasional cross-hybridization, and makes it so all oligonucleotides do not have to hybridize identically in order to obtain quantitative information. To further increase the sensitivity and specificity of detection, each complementary oligonucleotide (perfect match, or PM) is synthesized with a closely related mismatch (MM) partner in a physically adjacent position. The mismatch partner is identical except for a single base difference at the central position of the 25-mer. The MM oligonucleotide of each pair serves as an internal control that allows consistent hybridization patterns (patterns of PM signals that are larger than the corresponding MM signals) to be recognized. Quantitative image analysis is based on the average of the differences between the PM and MM partners, so that nonspecific and background contributions tend to cancel, while specific hybridization signals tend to add constructively across the set of oligonucleotide pairs for each gene. These hybridization signals are quantitative over three orders of magnitude, from 1:300,000 to 1:300.

TABLE 1

| | Candidate WT1 Targets |
|---|---|
| M59807 | NATURAL KILLER CELLS PROTEIN 4 PRECURSOR (HUMAN);contains element MSR1 repetitive element;. |
| M25317 | Human folate binding protein (FBP) mRNA, 3' end. |
| X06956 | Human HALPHA44 gene for alpha-tubulin, exons 1–3. |
| X51758 | Human mRNA for heat shock protein HSP70B'. |
| H17969 | *H. sapiens* mRNA for 90K product. |
| T66307 | HEAT SHOCK 70 KD PROTEIN 1 (HUMAN);. |
| M30704 | Human amphiregulin (AR) mRNA, complete cds, clones lambda-AR1 and lambda-AR2. |
| T51558 | PROCOLLAGEN ALPHA 1(I) CHAIN PRECURSOR (HUMAN). |
| M14083 | Human beta-migrating plasminogen activator inhibitor I mRNA, 3' end. |
| X05978 | Human radiated keratinocyte mRNA for cysteine protease inhibitor. |
| Z18951 | *H. sapiens* mRNA for caveolin. |

TABLE 1-continued

Candidate WT1 Targets

| | |
|---|---|
| M31776 | Human brain natriuretic protein (BNP) gene, complete cds. |
| L20859 | Human leukemia virus receptor 1 (GLVR1) mRNA, complete cds. |
| R71876 | KERATIN, TYPE I CYTOSKELETAL 17 (HUMAN);. |
| H45051 | TUBULIN ALPHA-5 CHAIN (*Gallus gallus*) |
| T47964 | PURINE NUCLEOSIDE PHOSPHORYLASE (HUMAN). |
| U10550 | Human Gem GTPase (gem) mRNA, complete cds. |
| D14874 | Human mRNA for adrenomedullin, complete cds. |
| R38636 | UROKINASE PLASMINOGEN ACTIVATOR SURFACE RECEPTOR, GPI-ANCHORED (HUMAN);. |
| X13097 | Human mRNA for tissue type plasminogen activator. |
| M96322 | Human gravin (a cytoplasmic antigen recognized by myasthenia gravis sera) mRNA, 3' end. |
| X51345 | Human jun-B mRNA for JUN-B protein. |
| X70940 | *H. sapiens* mRNA for elongation factor 1 alpha-2. |
| R16077 | HOMEOTIC GENE REGULATOR (Drosophila melanogaster) |
| X57348 | *H. sapiens* mRNA (clone 9112). |
| M26683 | Human interferon gamma treatment inducible mRNA. |
| Z17227 | *H sapiens* mRNA for transmembrane receptor protein. |
| R49231 | MITOCHONDRIAL PHOSPHATE CARRIER PROTEIN PRECURSOR (HUMAN);. |

TABLE 3

EWS

| | |
|---|---|
| R60906 | PROBABLE NUCLEAR ANTIGEN (Pseudorabies virus) |
| M26062 | INTERLEUKIN-2 RECEPTOR BETA CHAIN PRECURSOR (HUMAN);. |
| H20529 | G1/S-SPECIFIC CYCLIN D1 (*Homo sapiens*) |
| T79475 | PROBABLE NUCLEAR ANTIGEN (Pseudorabies virus) |
| M22349 | Human neuron-specific gamma-2 enolase, complete cds. |
| L49054 | *Homo sapiens* t(3;5)(q25.1;p34) fusion gene NPM-MLFI mRNA, complete cds. |
| H62466 | COLLAGEN ALPHA 3(VI) CHAIN (Gallus gallus) |
| U23852 | Human T-lymphocyte specific protein tyrosine kinase p56lck (lck) abberant mRNA, complete cds. |
| U20982 | Human insulin-like growth factor binding protein-4 (IGFBP4) gene, promoter and complete cds. |
| L16510 | *Homo sapiens* cathepsin B mRNA, complete cds. |
| T51534 | CYSTATIN C PRECURSOR (HUMAN). |
| R42291 | DUAL SPECIFICITY MITOGEN-ACTIVATED PROTEIN KINASE KINASE 2 (*Homo sapiens*) |
| T53118 | NEURONAL-GLIAL CELL ADHESION MOLECULE PRECURSOR (Gallus gallus) |
| H10925 | PIM-1 PROTO-ONCOGENE SERINE/THREONINE-PROTEIN KINASE (Mus musculus) |
| R54359 | CARBOXYLESTERASE PRECURSOR (Mus musculus) |
| L11329 | PROTEIN-TYROSINE PHOSPHATASE PAC-1 (HUMAN);. |
| X02492 | INTERFERON-INDUCED PROTEIN 6-16 PRECURSOR (HUMAN);contains L1 repetitive element;. |

What is claimed is:

1. A method for detecting a WT1 gene functional mutation in target cells comprising the steps of:

detecting expression of at least one down-stream gene of WT1 in a sample of (a) target cells, and (b) reference cells having a wild-type WT1 gene, wherein the reference cells are otherwise substantially similar to the target cells, the down-stream genes are up- or down-regulated by the wild-type WT1 gene, wherein said down-stream genes comprise at least one WT1 up-regulated gene selected from the group consisting of: natural killer cells protein 4 precursor (M59807), folate binding protein (M25317), HALPHA44 gene for alpha-tubulin (X06956), 90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1 ) (L20859), type 1 cytoskeletal 17 keratin (R71870), tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B(X51345), homeotic gene regulator (R16977), clone 9112 (X57348), interferon gamma treatment inducible mRNA (M26683), transmembrane receptor protein (Z17227) and mitochondrial phosphate carrier protein (R49231), and wherein said WT1 down-regulated gene is elongation factor 1 alpha-2 (X79490); and comparing the expression of the down-stream genes in the target cells and the reference cells, wherein a difference in the expression between the target cells and reference cells suggests a WT1 functional mutation in the target cells.

2. The method of claim 1, wherein said down-stream genes are transcriptionally regulated by said wild-type WT1 gene and the expression of said down-stream genes is detected by measuring amounts of transcripts of said down-stream genes in said reference and target cells.

3. The method of claim 1, wherein said amounts of transcripts are measured with a high-density nucleic acid array.

4. The method of claim 1, wherein said down-stream genes comprise at least three WT1 up-regulated genes selected from the group consisting of: natural killer cells protein 4 precursor (M59807), folate binding protein

TABLE 2

Genes Induced or Repressed by WT1

| Gene | Gene Class | Fold Induction | Previous Cancer Link |
|---|---|---|---|
| Alpha-Tubulin | Cytoskeletal | 12 | Migration, Invasion |
| Tissue Plasminogen Activator | Protease System | 4 | Migration, Invasion, metastasis |
| Urokinase Plasminogen Activator Inhibitor | Protease System | 4 | Migration, Invasion, metastasis |
| Urokinase Plasminogen Activator Receptor | Protease System | 3 | Migration, Invasion, metastasis |
| Cystatin | Protease System | 6 | Adherence, motility, levels correlated with cancer prognosis |
| Caveolin | Membrane | (−4) | Anchorage-independent growth |
| Amphiregulin | Growth Factor | 8 | Neoplasia, invasion, metastasis |
| Mac-2 Binding Protein | Secreted | 8 | Cell adhesion, secreted by many tumors |
| Folate Receptor | Receptor | 10 | Overexpressed in 90% of ovarian cancers, enhances tumor growth |
| GEM | Guanine Nucleotide Binding | 4 | Induced by oncogene-mediated tranformation |

(M25317), HALPHA44 gene for alpha-tubulin (X06956), 90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin (R71870), tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B(X51345), homeotic gene regulator (R16977), clone 9112 (X57348), interferon gamma treatment inducible mRNA (M26683), transmembrane receptor protein (Z17227) and mitochondrial phosphate carrier protein (R49231).

5. The method of claim 1 wherein expression of elongation factor 1 alpha-2 (X79490) is detected.

6. The method of claim 4 wherein expression of down-stream genes p21 or EGFR is additionally detected.

7. The method of claim 1 further comprising the step of:
   indicating a loss of function mutation in the WT1 gene in the target cells if the expression of said WT1 up-regulated genes is at least two times less in said target cells than in said reference cells or if the expression of said WT1 down-regulated gene is at least two times more in said target cells than in said reference cells.

8. A method for detecting a EWS-WT1 gene fusion in target cells comprising the steps of:
   detecting expression of one or more down-stream genes of an EWS-WT1 fusion in a sample of (a) target cells, and (b) reference cells having a wild-type EWS and WT1 gene, said reference cells being otherwise substantially similar to said target cells, said down-stream genes being up- or down-regulated by said EWS-WT1 fusion; and
   comparing the expression of said down-stream genes in said target cells and said reference cells, wherein a difference in said expression between the target cells and reference cells suggests a EWS-WT1 fusion in the target cells.

9. The method of claim 8, wherein said down-stream genes comprise at least one EWS-WT1 up-regulated gene selected from the group consisting of: Pseudorabies virus nuclear antigen (R60906 and T79475), beta chain of interleukin-2 receptor (M26062), G1/S-specific cyclin D1 (H20529), neuron-specific gamma-2 enolase (M22349), fusion gene NPM-MLF1 resulting from translocation t(3;5)(q25.1;p34) (L49054), collagen alpha 3(IV) chain (H62466), T-lymphocyte specific protein tyrosine kinase p561 ck(1 ck) (U23852), insulin-like growth factor binding protein-4 (U20982), cathepsin B (L16510), cystatin C (T51534), dual specificity mitogen-activated protein kinase kinase 2 (R42291), neuronal-glial cell adhesion molecule (T53118), PIM-1 proto-oncogene serine/threonine-protein kinase (H10925), carboxylesterase precursor (R54359), protein-tyrosine phosphatase PAC-1 (L11329), and interferon-induced protein 6–16 (X02492).

10. A functional assay for a WT1 sequence alteration comprising the steps of:
    detecting expression of at least one down-stream gene in a target sample from target cells having a WT1 sequence alteration and in a reference sample from reference cells having a wild-type WT1 gene, said reference cells being otherwise substantially similar to said target cells, said down-stream genes being up- or down-regulated by said wild-type WT1 gene, wherein said down-stream genes comprise at least one WT1 up-regulated gene selected from the group consisting of: natural killer cells protein 4 precursor (M59807), folate binding protein (M25317), HALPHA44 gene for alpha-tubulin (X06956), 90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin (R71870), tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), homeotic gene regulator (R16977), clone 9112 (X57348), interferon gamma treatment inducible mRNA (M26683), transmembrane receptor protein (Z17227) and mitochondrial phosphate carrier protein (R49231) or at least one WT1 down-regulated gene which is elongation factor 1 alpha-2 (X79490); and
    comparing said expression in said target sample to said expression in said reference sample, wherein a difference in the expression between said two samples suggests that said WT1 sequence alteration affects the biological function of WT1.

11. The method of claim 10, wherein said down-stream genes are transcriptionally regulated by said wild-type WT1 gene and the expression of said down-stream genes is detected by measuring amounts of transcripts of said down-stream genes in said reference and target cells.

12. The method of claim 11, wherein said amounts of transcripts are measured with a high-density nucleic acid array.

13. The method of claim 10, wherein said down-stream genes comprise at least three WT1 up-regulated genes selected from the group consisting of: natural killer cells protein 4 precursor (M59807), folate binding protein (M25317), HALPHA44 gene for alpha-tubulin (X06956), 90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin, tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), homeotic gene regulator (R16977), clone 9112 (X57348), interferon gamma treatment inducible mRNA (M26683), transmembrane receptor protein (Z17227) and mitochondrial phosphate carrier protein(R49231).

14. The method of claim 10 wherein said down-stream genes comprise at least one WT1 down-regulated gene which is elongation factor 1 alpha-2 (X79490).

15. The method of claim 13 wherein expression is also detected of down-stream genes p21 or EGFR.

16. The method of claim 10 further comprising the steps of:
    indicating that said WT1 sequence alteration is a loss of wild-type function mutation if the expression of said WT1 up regulated genes is at least two times less in said target cells than in said reference cells or if the expression of said WT1 down regulated genes is at least two times more in said target cells than in said reference cells.

17. A method for detecting a mutation in a target WT1 gene using a computer comprising:
inputting into a computer wild-type cell expression data of at least one down-stream gene in a wild-type sample containing a wild-type WT1 gene, said down-stream genes being transcriptionally regulated by said wild-type WT1 gene, wherein said down-stream genes comprise at least one WT1 up-regulated gene selected from the group consisting of: natural killer cells protein 4 precursor (M59807), folate binding protein (M25317), HALPHA44 gene for alpha-tubulin (X06956), 90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin (R71870), tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B(X51345), homeotic gene regulator (R16977), clone 9112 (X57348), interferon gamma treatment inducible mRNA (M26683), transmembrane receptor protein (Z17227) and mitochondrial phosphate carrier protein (R49231), or WT1 down-regulated gene elongation factor 1 alpha-2 (X79490);
inputting into a computer target cell expression data of said plurality of down-stream genes in a target sample containing said target WT1 gene;
comparing the target and wild-type expression data to determine differences, wherein differences suggest a mutation in said target WT1 gene.

18. The method of claim 17, wherein said down-stream genes comprise at least three WT1 up-regulated genes selected from the group consisting of: natural killer cells protein 4 precursor (M59807), folate binding protein (M25317), HALPHA44 gene for alpha-tubulin (X06956),90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin, tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), homeotic gene regulator (R16977), clone 9112 (X57348), interferon gamma treatment inducible mRNA (M26683), transmembrane receptor protein (Z17227) and mitochondrial phosphate carrier protein H(R49231).

19. The method of claim 17 wherein expression data of said down-stream gene elongation factor 1 alpha-2 (X79490) is input.

20. The method of claim 18 wherein wild-type and target cell transcriptional expression data of down-stream genes p21 or EGFR are also input into the computer.

21. The method of claim 17 further comprising the step of:
indicating a mutation in said target WT1 gene if the expression of said WT1 up-regulated genes is at least two times less in said target cells than in said wild-type cells or if the expression of said WT1 down-regulated genes is at least two times more in said target cells than in said wild-type cells.

22. A method for detecting a translocation fusing EWS and WT1 genes using a computer comprising:
inputting into a computer wild-type cell expression data of a plurality of down-stream genes in a wild-type sample containing wild-type EWS and WT1 genes, said down-stream genes being transcriptionally regulated by a EWS-WT1 fusion protein;
inputting into a computer target cell expression data of said plurality of down-stream genes in a target sample being tested for the presence of a EWS-WT1 fusion protein;
comparing the target and wild-type expression data to determine differences, wherein differences suggest a translocation fusing the EWS and WT1 genes.

23. The method of claim 22, wherein said down-stream genes comprise at least one EWS-WT1 up-regulated gene selected from the group consisting of: Pseudorabies virus nuclear antigen (R60906 and T79475), beta chain of interleukin-2 receptor (M26062), G1/S-specific cyclin D1 (H20529), neuron-specific gamma-2 enolase (M22349), fusion gene NPM-MLF1 resulting from translocation t(3;5)(q25.1;p34) (L49054), collagen alpha 3(IV) chain (H62466), T-lymphocyte specific protein tyrosine kinase p561 ck(1 ck) (U23852), insulin-like growth factor binding protein-4 (U20982), cathespsin B, cystatin C (T51534), dual specificity mitogen-activated protein kinase kinase 2 (R42291), neuronal-glial cell adhesion molecule (T53118), PIM-1 proto-oncogene serine/threonine-protein kinase (H10925), carboxylesterase precursor (R54359), protein-tyrosine phosphatase PAC-1 (L11329), and interferon-induced protein 6–16 (X02492).

24. A method for detecting a WT1 gene functional mutation in target cells comprising the steps of:
detecting transcriptional expression of at least one down-stream gene of WT1 in a sample of (a) target cells, and (b) reference cells having a wild-type WT1 gene, said reference cells being otherwise substantially similar to said target cells, said down-stream gene being selected from the group consisting of: natural killer cells protein 4 precursor (M59807), folate binding protein (M25317), HALPHA44 gene for alpha-tubulin (X06956), 90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin (R71870), tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), elongation factor 1 alpha-2 (X79490), homeotic gene regulator (R16977), clone 9112 (X57348), interferon gamma treatment inducible mRNA (M26683), and transmembrane receptor protein (Z17227) mitochondrial phosphate carrier protein (R49231), and caveolin; and
comparing the transcriptional expression of said at least one down-stream gene in said target cells and said reference cells, wherein a difference in said expression between the target cells and reference cells suggests a WT1 functional mutation in the target cells.

25. A functional assay for a WT1 sequence alteration comprising the steps of:

detecting transcriptional expression of at least one downstream gene selected from the group consisting of: natural killer cells protein 4 precursor (M59807), folate binding protein (M25317), HALPHA44 gene for alpha-tubulin (X06956), 90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin, tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), elongation factor 1 alpha-2 (X79490), homeotic gene regulator (R16977), clone 9112 (X57348), interferon gamma treatment inducible mRNA (M26683), transmembrane receptor protein (Z17227), caveolin and mitochondrial phosphate carrier protein (R49231) in a target sample from target cells having a WT1 sequence alteration and in a reference sample from reference cells having a wild-type WT1 gene, said reference cells being otherwise substantially similar to said target cells, said down-stream genes being up- or down-regulated by said wild-type WT1 gene; and comparing said transcriptional expression in said target sample to said transcriptional expression in said reference sample, wherein a difference in the expression between said two samples suggests that said WT1 sequence alteration affects the biological function of WT1.

26. A method for detecting a mutation in a target WT1 gene using a computer comprising:

inputting into a computer wild-type cell transcriptional expression data of at least one WT1-down-stream gene in a wild-type sample containing a wild-type WT1 gene, wherein said down-stream gene is selected from the group consisting of: natural killer cells protein 4 precursor (M59807), folate binding protein (M25317), HALPHA44 gene for alpha-tubulin (X06956), 90 K product (H17969), amphiregulin (M30704), procollagen alpha 1 (T51558), beta-migrating plasminogen activator inhibitor 1 (M14083), cysteine protease inhibitor from radiated keratinocytes (X05978), brain natriuretic protein (BNP) (M31766), leukemia virus receptor 1 (GLVR1) (L20859), type 1 cytoskeletal 17 keratin, tubulin alpha-5 chain (H45051), purine nucleoside phosphorylase (T47964), Gem GTPase (U10550), adrenomedullin (D14874), GPI-anchored urokinase plasminogen activator surface receptor (R38636), tissue type plasminogen activator (X13097), gravin (M96322), jun-B (X51345), elongation factor 1 alpha-2 (X79490), homeotic gene regulator (R 16977), clone 9112 (X57348), interferon gamma treatment inducible mRNA (M26683), transmembrane receptor protein (Z17227), caveolin, and mitochondrial phosphate carrier protein (R49231); and inputting into a computer target cell transcriptional expression data of said plurality of down-stream genes in a target sample containing said target WT1 gene;

comparing the target and wild-type expression data to determine differences, wherein differences suggest a mutation in said target WT1 gene.

\* \* \* \* \*

UNITED STATES PATENT AND TRADEMARK OFFICE
CERTIFICATE OF CORRECTION

PATENT NO. : 6,177,248 B1
DATED : January 23, 2001
INVENTOR(S) : Jonathan Oliner et al.

It is certified that error appears in the above-identified patent and that said Letters Patent is hereby corrected as shown below:

Column 1,
Lines 45 and 56, after "embodiment" -- , -- has been inserted,
Line 49, "substantial" has been replaced with -- substantially --, Column 2,
Line 23, after "embodiment" -- , -- has ben inserted.

Column 7,
Line 16, "A n" has been replaced with -- an --,
Line 24, after "Thus" -- , -- has been inserted,
Line 25, after "example" -- , -- has been inserted,
Line 62, "C." has been replaced with -- C --, Column 8,
Line 10, "C." has been replaced with -- C --,
Lines 18 and 21, after "e.g." -- , -- has been inserted, Column 11,
Line 39, "of" has been deleted, Column 13,
Line 11, "ie." has been replaced with -- i.e., --, Column 16,
Line 46, "methods" has been replaced with -- method --,

UNITED STATES PATENT AND TRADEMARK OFFICE
CERTIFICATE OF CORRECTION

PATENT NO.    : 6,177,248 B1
DATED         : January 23, 2001
INVENTOR(S)   : Jonathan Oliner et al.

It is certified that error appears in the above-identified patent and that said Letters Patent is hereby corrected as shown below:

<u>Column 17,</u>
Line 29, "application" has been replaced with -- Application --,
Line 29, "1994now" has been replaced with -- 1994 now --.

Signed and Sealed this

First Day of January, 2002

Attest:

Attesting Officer

JAMES E. ROGAN
*Director of the United States Patent and Trademark Office*